United States Patent [19]

Mondadori et al.

[11] 4,431,641
[45] Feb. 14, 1984

[54] PHARMACEUTICAL COMPOSITIONS HAVING ANTIEPILEPTIC AND ANTINEURALGIC ACTION

[75] Inventors: Cesare Mondadori, Don Mills, Canada; Markus Schmutz, Basel, Switzerland

[73] Assignee: Ciba-Geigy Corporation, Ardsley, N.Y.

[21] Appl. No.: 310,197

[22] Filed: Oct. 9, 1981

[30] Foreign Application Priority Data

Oct. 17, 1980 [CH] Switzerland ................. 7775/80

[51] Int. Cl.³ .................. A61K 31/33; A61K 31/40; A61K 31/44; A61K 31/475
[52] U.S. Cl. ........................... 424/244; 424/262; 424/263; 424/274
[58] Field of Search ................. 424/244, 274

[56] References Cited

U.S. PATENT DOCUMENTS 4,076,812  2/1978  Allgeir et al. ..

OTHER PUBLICATIONS

Martin Negwer: Organisch-chemische Arzneimittel and Ihre Synonyma 5 Edition, vol. 1, p. 487 (1978).
Dictionaire Vidal: Edition 1982, p. 893.
Chem. Abst. 92, 34353g (1980).
Chem. Abstract, 72 41379k (1972).
B. M. Kulig et al., Adv. Epileptol, Proc. Comgr. Int. League Epilepsey, 13th (1977) pp. 89–103/CA9-0-11515e.
Jacobides, G. M., Adv. Epileptol, Proc. Congr. Int. League Epilepsey, 13th, 1977 pp. 114–119 CA 90-11539N.
S. J. Sara et al., Psychopharmacologia 25, 32–40 (1972).
Boggan et al., Behavioral Biology, 12 127—134 (1974).

*Primary Examiner*—Stanley J. Friedman
*Attorney, Agent, or Firm*—Irving N. Feit

[57] ABSTRACT

The present invention relates to novel pharmaceutical compositions having antiepileptic and antineuraglic action and containing (a) at least one anticonvulsive compound of the general formula I

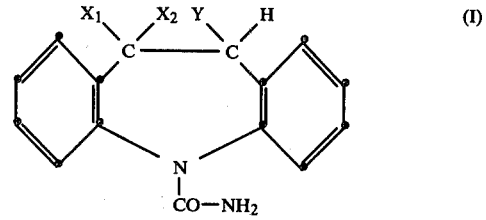

wherein $X_1$ is hydrogen, halogen having an atomic number up to 35, or is cyano, and $X_2$ and Y together are an additional bond, or $X_1$ and $X_2$ together are the oxo radical, or $X_1$ is hydroxy, $X_2$ is hydrogen and Y is also hydrogen, and (b) at least one nootropic compound of the vincamine type which has the general formula II

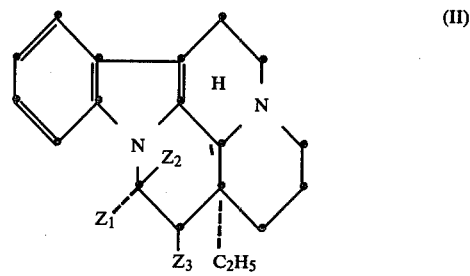

wherein $Z_1$ is lower alkoxycarbonyl, $Z_2$ is hydroxy and $Z_3$ is hydrogen, or $Z_2$ and $Z_3$ together are an additional bond, or one of $Z_1$ and $Z_2$ is hydroxy and the other is hydrogen and $Z_3$ is also hydrogen, in particular vincamine (DCI rec.), in which $Z_1$ is methoxycarbonyl, $Z_2$ is hydroxy and $Z_3$ is hydrogen, and also e.g., vinpocetin (DCI rec.), in which $Z_1$ is ethoxycarbonyl and $Z_2$ and $Z_3$ together form an additional bond, as well as vincanol (DCI prop.), in which one of $Z_1$ and $Z_2$ is hydroxy and the other is hydrogen and $Z_3$ is hydrogen, and the acid addition salts thereof, or at least one nootropic derivative of 2-pyrrolidinone, e.g. 2-oxo-1-pyrrolidineaetamide (piracetam) or one of its nootropic derivatives. The compounds of the general formula II e.g. vincamine, as well as the nootropic derivatives of 2-pyrrolidinone, e.g. piracetam, have in themselves virtually no anticonvulsive activity but potentiate the action of the compounds of the general formula I, e.g. carbamazepine.

14 Claims, No Drawings

PHARMACEUTICAL COMPOSITIONS HAVING ANTIEPILEPTIC AND ANTINEURALGIC ACTION

The present invention relates to novel pharmaceutical compositions having antiepileptic and antineuralgic action and containing at least one specific compound with corresponding properties and at least one second compound which potentiates the action of the first compound, and to the administration of said compositions.

Surprisingly, it has been found that the anticonvulsive action of compounds of the general formula I

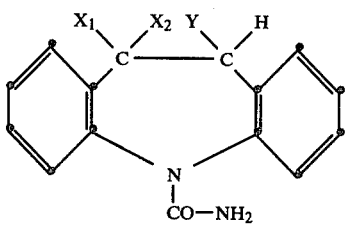

wherein $X_1$ is hydrogen, halogen having an atomic number up to 35, or is cyano, and $X_2$ and Y together are an additional bond, or $X_1$ and $X_2$ together are the oxo radical, or $X_1$ is hydroxy, $X_2$ is hydrogen and Y is also hydrogen, is potentiated by nootropic compounds of the vincamine type which, in themselves alone, have virtually no anticonvulsive action, and which have the general formula II

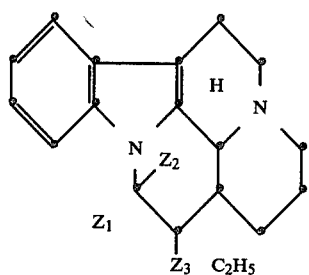

wherein $Z_1$ is lower alkoxycarbonyl, $Z_2$ is hydroxy and $Z_3$ is hydrogen, or $Z_2$ and $Z_3$ together are an additional bond, or one of $Z_1$ and $Z_2$ is hydroxy and the other is hydrogen and $Z_3$ is also hydrogen, in particular vincamine (DCI rec.), in which $Z_1$ is methoxycarbonyl, $Z_2$ is hydroxy and $Z_3$ is hydrogen, and also e.g., vinpocetin (DCI rec.), in which $Z_1$ is ethoxycarbonyl and $Z_2$ and $Z_3$ together form an additional bond, as well as vincanol (DCI prop.), in which one of $Z_1$ and $Z_2$ is hydroxy and the other is hydrogen and $Z_3$ is hydrogen, and the acid addition salts thereof; and also by nootropic, but in themselves not anticonvulsive, derivatives of 2-pyrrolidinone, e.g. 2-oxo-1-pyrrolidineacetamide (piracetam) and its derivatives, e.g. those of the general formula III

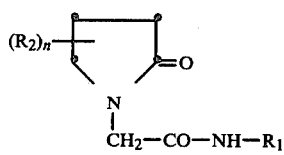

wherein $R_1$ is hydrogen, lower alkyl, (di-lower alkylamino)-lower alkyl, 2-(2,6-dimethylpiperidino)ethyl, carbamoylmethyl or the radical of the formula

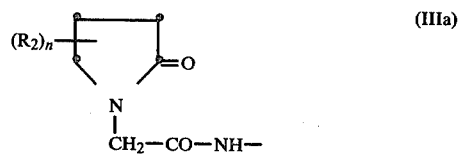

$R_2$ is lower alkyl, preferably methyl, and n is 0 or an integer from 1 to 4, but is preferably 0 or 1, and, if $R_1$ is hydrogen and n is 1, $R_2$ can also be hydroxy, while compounds of this type, wherein n is different from 0, can be in the form of mixtures of stereoisomers, racemates or pure optically active antipodes.

The potentiating action of compounds of the general formula II, especially of vincamine, on compounds of the general formula I, can be observed e.g. in the electroshock test on rats by oral administration of increasing doses of 1, 3, 6, 10 and 30 mg/kg of anticonvulsive compound of the formula I, such as carbamazepine, without and together with increasing doses of 1, 3, 10, 30 and 100 mg/kg of a compound of the formula II, such as vincamine, and by determining the protective action (prevention of convulsion) against electroshock one hour after administration of the compounds, or combination thereof, to be tested. In these assays, the addition of the, by itself, virtually inactive amount of 1 to 30 mg/kg of vincamine to carbamazepine, e.g. in the dosage range of 3 to 10 mg/kg of the latter, reduces the doses of carbamazepine which are of equal effectiveness to about half; or, when equal doses of carbamazepine without and together with vincamine are compared, a substantially increased protective action is attained. A reduction of the doses of carbamazepine of equal effectiveness in the dosage range from 3 to 10 mg/kg per os, is also reduced to about half in the same test, e.g. by the simultaneous administration of piracetam, which is by itself completely inactive, as representative of the nootropic derivatives of 2-pyrrolidinone, in doses of 10 to 1000 mg/kg per os, especially of 30 to 300 mg/kg per os.

In learning assays with rats, i.e. in an active avoidance test (one way platform jumps) with Ra 25, IN-VANOVAS rats (weight: 180–200 g), the learning performance of animals to each of which daily 30 mg/kg of carbamazepine were administered per os as solid and 3 mg/kg of vincamine hydrochloride i.p. as aqueous solution, was about the same as the learning performance of control animals to which there were administered, instead of the active ingredients, methocel per os and sodium chloride solution i.p.

On the basis of the pharmacological findings indicated above, the present invention accordingly provides pharmaceutical compositions which contain (a) at least one compound of the above defined general formula I, and (b) at least one compound of the above indicated general formula II, and/or at least one pharmaceutically acceptable acid addition salt thereof, or at least one nootropic derivative of 2-pyrrolidinone, with or without pharmaceutical carriers and excipients, and which compositions, like the compounds of the general formula I contained therein, possess antiepileptic and antineuralgic activity.

The ratios of the compounds of formula I to the compounds of formula II, or to the pharmaceutically acceptable acid addition salts of these latter, are from about 5:1 to about 100:1, preferably from about 10:1 to about 75:1, and, most preferably, from about 20:1 to about 50:1. Dosage units for oral administration, such as tablets, dragées or capsules, contain both active ingredients preferably in amounts which are suitable for the daily administration of about 300 to about 1200 mg of a compound of the general formula I, and about 3 to about 60 mg, preferably about 6 to about 12 mg, of a compound of the general formula II, as base or in the form of a pharmaceutically acceptable acid addition salt, to adults of normal weight, or of correspondingly reduced doses to children, once to three times. Such amounts are about 25 to about 300 mg, preferably about 50 to about 200 mg, of a compound of the general formula I, and about 1 to about 20 mg, preferably about 1 to about 5 mg, of a compound of the general formula II, e.g. vincamine, as base or salt.

The ratios of compounds of the general formula I to nootropic derivatives of 2-pyrrolidinone, e.g. compounds of the general formula III, are about 1:1 to about 1:8, and preferably about 1:1.5 to about 1:4. Dosage units for oral administration, such as tablets, dragées or capsules, contain both active ingredients preferably in amounts which are suitable for oral administration of again about 300 to about 1200 mg of a compound of formula I, and about 300 to about 2400 mg, and preferably about 600 to about 1200 mg, of a nootropic derivative of 2-pyrrolidinone, e.g., a compound of formula III, to human adults of normal weight, which are in need of such treatment, or of correspondingly reduced doses to children, 1 to 3, preferably 2, dosage units being taken once to three times. Such amounts are about 25 to about 300 mg, preferably about 50 to about 200 mg, of a compound of the formula I, and about 100 to about 600 mg, preferably about 100 to about 400 mg, of a nootropic derivative of 2-pyrrolidinone, e.g. piracetam.

The ratios and amounts specified above apply not only to a single compound of the type in question, but also to the total amounts of several compounds of the same type.

The invention comprises also the separate, but substantially simultaneous oral administration of (a) a compound of the general formula I as defined above, e.g. carbamazepine, and (b) a compound of the general formula II as defined above, e.g. vincamine, or a pharmaceutically acceptable acid addition salt thereof, or a nootropic derivative of 2-pyrrolidinone, e.g. 2-oxo-1-pyrrolidineacetamide (piracetam) and its derivatives, e.g. those of the general formula III as defined above, in the doses indicated above, to a human being in need of such treatment.

Divisible dosage units, such as tablets with breaking notch and those with delayed release of the active ingredient, can also contain larger amounts of active ingredient.

Formulations for oral administration which are not in dosage unit form, such as syrups, contain the active ingredients in suitable amount, especially in suitable volume units of e.g. 2.5 or 5 ml, for example about 25 to about 100 mg of a compound of the general formula I and about 1 to about 10 mg of a compound of the general formula II, preferably in the form of a pharmaceutically acceptable acid addition salt, or about 100 to 600 mg, preferably about 100 to 400 mg, of a nootropic derivative of 2-pyrrolidinone, e.g. a compound of the general formula III.

In addition to carbamazepine (5H-dibenz[b,f]azepine-5-carboxamide), examples of suitable compounds of the general formula I are: 10-oxo-10,11-dihydro-5H-dibenz[b,f]azepine-5-carboxamide (cf. U.S. Pat. No. 3,643,775) and 10-hydroxy-10,11-dihydro-5H-dibenz[b,f]azepine-5-carboxamide (cf. U.S. Pat. No. 3,367,667) as well as 10-fluoro-, 10-chloro- and 10-bromo-5H-dibenz[b,f]azepine-5-carboxamide (cf. U.S. Pat. No. 4,076,812), and 10-cyano-5H-dibenz[b,f]azepine-5-carboxamide (cf. European Patent application No. 11.603).

In the compounds of the general formula II, lower alkoxycarbonyl contains 1 to 7, preferably 1 to 5, carbon atoms, and is e.g. propoxycarbonyl, isopropoxycarbonyl, butoxycarbonyl, isobutoxycarbonyl, pentyloxycarbonyl, isopentyloxycarbonyl, neopentyloxycarbonyl or hexyloxycarbonyl, but preferably methoxycarbonyl or ethoxycarbonyl.

Suitable compounds of the general formula II are, in addition to vincamine, for example the two compounds already referred to above, vinpocetin (DCI rec.) and vincanol (DCI prop.). Examples of suitable acid addition salts of the compounds of the general formula II, e.g. of the three compounds just mentioned, are those with hydrochloric acid, hydrobromic acid, phosphoric acid, methanesulfonic acid, ethanesulfonic acid, acetic acid, lactic acid, succinic acid, fumaric acid, maleic acid, malic acid, tartaric acid, citric acid, benzoic acid, salicylic acid, phenylacetic acid, mandelic acid and embonic acid.

Suitable nootropic derivatives of 2-pyrrolidinone are, e.g., 1-(4-methoxybenzoyl)-2-pyrrolidinone (aniracetam) and 2-oxo-1-pyrrolidineacetamide (piracetam) and derivatives thereof, in particular such derivatives which, like piracetam, correspond to the formula III, e.g. amacetam, in which n is 0 and $R_1$ is 2-(diisopropylamino)-ethyl, further the compound in which n is 0 and $R_1$ is 2-(2,6-dimethylpiperidino)-ethyl, and the compound in which $R_1$ is hydrogen, n is 1 and $R_2$ is hydroxy in the 4-position of the pyrrolidine ring, or compounds of the formula III in which $R_1$ is a radical of the formula IIIa, such as dupracetam, wherein n is 0, or the corresponding compound wherein in each half of the formula n is 1 and $R_2$ is methyl in the 5-position of both pyrrolidine rings.

The pharmaceutical compositions of this invention are mainly suitable for treating the same conditions as the compounds of the general formula I contained therein. In particular, they are suitable for the treatment of epileptic conditions such as partial convulsions with complex or simple symptomatology, primary and secondary generalized convusions with tonic-clonic component, and mixed convulsions, and an adjuvants in the case of generalized convulsions of the absence-type (petit mal). Further they are suitable for the treatment of genuine trigeminal neuralgia and trigeminal neuralgia due to multiple sclerosis, genuine glossopharyngeal neuralgia, alcohol withdrawal syndrome, diabetes insipidus centralis, mania and certain forms of depression.

The above conditions are treated by the oral administration of therapeutically effective amounts of the pharmaceutical compositions of this invention to human beings in need of such treatment. In particular, these compositions are administered in amounts corresponding to daily doses of normally about 4 to 20 mg/kg of a compound of the general formula I and about 0.1 to about 1 mg/kg of a compound of the general formula II as base or in the form of a salt, or about 4 to about 40 mg/kg of a compound of the general formula III. For adult patients of normal weight, this corresponds to daily doses of about 300 to about 1200 mg of a compound of the general formula I and about 6 to about 60 mg of a compound of the general formula II as base or in the form of a salt, or about 300 to about 2400 mg of a nootropic derivative of 2-pyrrolidinone, e.g. 2-oxo-1-pyrrolidineacetamide or a derivative thereof, such as a compound of the general formula III, for treating the conditions specified above. On account of the reduction in doses of compounds of the general formula I resulting from the combination with compounds of the general formula II or with nootropic derivatives of 2-pyrrolidinone, the side effects can generally be diminished.

The pharmaceutical compositions of this invention contain effective antiepileptic and/or antineuralgic amounts of the indicated types of compounds, especially the amounts specified above, preferably together with inorganic or organic, solid or liquid, pharmaceutical carriers which are suitable for enteral, e.g. oral, administration. Tablets or dragées cores are prepared by combining the active ingredients e.g. with solid pulverulent carriers such as lactose, dextrose, saccharose, mannitol, sorbitol, cellulose and/or glycine, optionally with the addition of glidants and lubricants, e.g. silica, talcum, stearic acid or salts thereof, such as magnesium or calcium stearate, and/or polyethylene glycol, optionally with the addition of binders, e.g. magnesium aluminium silicate, starches such as corn, wheat, rice or arrow root starch, gelatin, tragacanth, methyl cellulose, sodium carboxymethylcellulose and/or polyvinyl-pyrrolidone, and, if desired, disintegrators, e.g. starches, agar, alginic acid or salts thereof, such as sodium alginate, and/or effervescent mixtures, or adsorpiton agents, colorants, flavouring matters and sweeteners. Dragée cores are coated e.g. with concentrated sugar solutions which may additionally contain e.g. gum arabic, talcum and/or titanium dioxide, or trouided with a shellac coating which is dissolved in readily volatile organic solvents or solvent mixtures. Colorants can be added to the coatings, for example to identify different doses of active ingredient.

Further dosage unit forms for oral administration are dry-filled capsules made from gelatin and soft sealed capsules made from gelatin and a plasticiser such as glycerol. The dry-filled capsules preferably contain a granular formulation of the active ingredient, e.g. in admixture with fillers such as corn starch, and/or with lubricants such as talcum or magnesium stearate, and, if desired, with stabilisers, e.g. ascorbic acid. In soft capsules the active ingredient is preferably dissolved or suspended in suitable liquids, e.g. liquid polyethylene glycols, to which stabilisers can also be added.

Suitable formulations which are not in dosage unit form are, in particular, syrups prepared in conventional manner which preferably contain a suspension of the compound of the general formula I and preferably a solution, but optionally also a suspension, of the compound of the general formula II or a pharmaceutically acceptable acid addition salt thereof.

The pharmaceutical compositions can be sterilised and/or contain adjuvants, e.g. preservatives, stabilisers, wetting agents and/or emulsifiers, solubilisers, salts for regulating the osmotic pressure, and/or buffers. The pharmaceutical compositions of the invention which, if desired, can contain further pharmacologically active substances, are prepared in a manner known per se, for example by conventional mixing, granulating, confectioning or dissolving methods, and they contain from about 10% to 100%, preferably from about 20% to 80%, of a combination according to the invention.

EXAMPLE 1

Tablets each containing 50 g of 5H-dibenz[b,f]azepine-5-carboxamide and 2 mg of vincamine hydrochloride can be prepared as follows:

| Composition (1000 tablets) | |
|---|---|
| 5H—dibenz[b,f]azepine-5-carboxamide | 500.0 g |
| vincamine hydrochloride | 20.0 g |
| lactose | 480.0 g |
| potato starch | 352.0 g |
| gelatin | 8.0 g |
| talcum | 60.0 g |
| magnesium stearate | 10.0 g |
| highly disperse silica | 20.0 g |
| ethanol | q.s. |

The two active ingredients are mixed with the lactose and 292 g of potato starch and the mixture is moistened with an alcoholic solution of the gelatin and granulated through a sieve. After drying, the remainder of the potato starch, the talc, magnesium stearate and the highly disperse silica are admixed and the mixture is compressed to tablets each weighing 145.0 mg. If desired, these tablets can be provided with a breaking notch for a finer adjustment of the dose.

Tablets containing 1 or 5 mg of vincamine hydrochloride can be prepared by using this compound in an amount of 10 g together with 490 g of lactose, or in an amount of 50 g together with 450 g of lactose.

EXAMPLE 2

Shellac coated tablets each containing 100 mg of 5H-dibenz[b,f]azepine-5-carboxamide and 5 mg of vincamine hydrochloride can be prepared as follows:

| Composition (for 1000 tablets) | |
|---|---|
| 5H—dibenz[b,f]azpine-5-carboxamide | 100.00 g |
| vincamine hydrochloride | 5.00 g |
| lactose | 95.00 g |
| corn starch | 70.00 g |
| talcum | 8.50 g |
| calcium stearate | 1.50 g |
| hydroxypropylmethylcellulose | 2.36 g |
| shellac | 0.64 g |
| water | q.s. |
| methylene chloride | q.s. |

The active ingredients, the lactose, and 40 g of the corn starch are mixed and the mixture is moistened with a starch paste prepared from 15 g of corn starch and water (with heating) and granulated. The granulate is dried and the remainder of the corn starch. The talc and teh calcium stearate are added to and mixed with the granulate. The mixture is compressed to tablets weighing 280 g and these are then coated with a solution of the hydroxypropylmethylcellulose and the shellac in methylene chloride. Final weight of the coated tablets: 283 mg.

Shellac coated tablets containing 1 mg or 10 mg of vincamine hydrochloride can be prepared by using this compound in an amount of 1 g together with 99 g of lactose, or in an amount of 10 g together with 90 g of lactose.

EXAMPLE 3

Shellac coated tablets each containing 50 mg of 5H-dibenz-[b,f]azepine-5-carboxamide and 100 mg of piracetam can be prepared as described in Example 2. Their composition is as follows:

| Composition (for 1000 tablets) | |
|---|---|
| 5H—dibenz[b,f]azepine-5-carboxamide | 50.00 g |
| piracetam | 100.00 g |
| lactose | 50.00 g |
| corn starch | 70.00 g |
| talcum | 8.50 g |
| calcium stearate | 1.50 g |
| hydroxypropylmethylcellulose | 2.36 g |
| shellac | 0.64 g |
| water | q.s. |
| methylene chloride | q.s. |

What is claimed is:

1. A pharmaceutical compositions comprising an antiepileptic amount of a combination of at least one compound of formula I as follows:

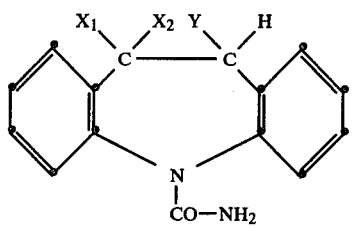

and an amount sufficient to potentiate the activity of the compound of formula I of at least one compound of formula III as follows:

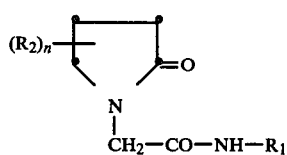

wherein $R_1$ is hydrogen, lower alkyl, (di-lower alkylamino)-lower alkyl, carbamoylmethyl or a radical of the formula

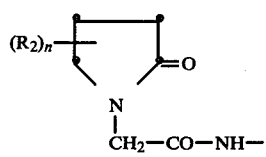

wherein $R_2$ is lower alkyl, n is 0 or an integer from 1–4, and, if $R_1$ is hydrogen and n is 1, $R_2$ is hydroxy.

2. A pharmaceutical composition according to claim 1 which contains 5H-dibenz[b,f]azepine-5-carboxamide as compound of formula I.

3. A pharmaceutical composition according to claim 1 which contains 10-oxo-10,11-dihydro-5H-dibenz[b,f]azepine-5-carboxamide as compound of formula I.

4. A pharmaceutical composition according to claim 1 which contains 10-hydroxy-10,11-dihydro-5H-dibenz[b,f]azepine-5-carboxamide as compound of formula I.

5. A pharmaceutical composition according to claim 1 which contains piracetam as compound of formula III.

6. A pharmaceutical composition according to claim 1 which contains 5H-dibenz[b,f]azepine-5-carboxamide and piracetam.

7. A pharmaceutical composition according to claim 1 which contains a compound of formula I and a compound of formula III in a ratio of about 1:1 to about 1:8.

8. A pharmaceutical composition according to claim 1 which contains a compound of formula I and a compound of the general formula III in a ratio of about 1:1.5 to about 1:6.

9. A pharmaceutical composition according to claim 1 which contains a compound of the general formula I in an amount of altogether about 25 to about 300 mg, and 2-oxo-1-pyrrolidineacetamide in an amount of altogether about 100 to about 600 mg, in a dosage unit or in a suitable amount of a formulation for oral administration which is not in dosage unit form.

10. A pharmaceutical composition according to claim 1 which contains a compound of the general formula I in an amount of about 25 to 300 mg, and a compound of the general formula III in an amount of about 100 to about 600 mg, in a dosage unit or in a suitable amount or a formulation for oral administration which is not in dosage unit form.

11. A pharmaceutical composition according to claim 1 which contains a compound of the general formula I in an amount about 50 to about 200 mg, and a compound of the general formula II, or a pharmaceutically acceptable acid addition salt thereof, in an amount of about 100 to about 600 mg, in a dosage unit or in a suitable amount of a formulation for oral administration which is not in dosage unit form.

12. A pharmaceutical composition according to claim 1 which contains about 50 to about 200 mg of 5H-dibenz[b,f]azepine-5-carboxamide and about 100 to about 400 mg of piracetam.

13. A pharmaceutical composition according to claim 1 which additionally contains at least one pharmaceutical carrier.

14. A method of treating epileptic conditions, by administering to a human being in need of such treatment a therapeutically effective amount of a composition according to claim 1.

* * * * *